(12) United States Patent
Paris et al.

(10) Patent No.: US 9,539,042 B2
(45) Date of Patent: Jan. 10, 2017

(54) SYRINGE FOR THE DELIVERY OF VISCOUS COMPOSITIONS

(75) Inventors: Michael W. Paris, Lansdale, PA (US); Theodore D. Clineff, Phoenixville, PA (US); Dean A. Entrekin, Downingtown, PA (US); Charanpreet S. Bagga, Phoenixville, PA (US); James P. Murphy, Newtown Square, PA (US)

(73) Assignee: Orthovita, Inc., Malvern, PA (US)

( * ) Notice: Subject to any disclaimer, the term of this patent is extended or adjusted under 35 U.S.C. 154(b) by 2183 days.

(21) Appl. No.: 12/057,603

(22) Filed: Mar. 28, 2008

(65) Prior Publication Data

US 2008/0243130 A1  Oct. 2, 2008

Related U.S. Application Data

(60) Provisional application No. 60/909,230, filed on Mar. 30, 2007, provisional application No. 60/921,207, filed on Mar. 30, 2007.

(51) Int. Cl.
*A61B 17/58* (2006.01)
*A61B 17/88* (2006.01)

(52) U.S. Cl.
CPC ........ *A61B 17/8822* (2013.01); *A61B 17/8825* (2013.01); *A61B 17/8827* (2013.01)

(58) Field of Classification Search
CPC ............ A61B 17/8822; A61B 17/8825; A61B 5/1433; A61M 5/16804; A61M 2005/1652; A61M 2005/2073

(Continued)

(56) References Cited

U.S. PATENT DOCUMENTS 3,223,083 A    12/1965  Cobey
4,685,910 A *   8/1987  Schweizer .................... 604/218

(Continued)

FOREIGN PATENT DOCUMENTS

EP    1 074 231 A1    2/2001
FR    2 690 332 A    10/1993

(Continued)

OTHER PUBLICATIONS

Gangi, A., et al. *Percutaneous Vertebroplasty Guided by a Combination of CT and Fluoroscopy*, AJNR 15:83-86, Jan. 1994.

(Continued)

*Primary Examiner* — Brian Pellegrino
(74) *Attorney, Agent, or Firm* — Lerner, David, Littenberg, Krumholz & Mentlik, LLP

(57) ABSTRACT

A syringe configured to deliver viscous compositions is described, in which the syringe may include an elongate chamber having side port(s) extending therefrom. Various viscous compositions may be inserted through the side port(s) and into the elongate chamber, which may further house a plunger for ejecting the composition. One portion of the plunger may interact with a restricted opening on the chamber to inhibit removal of the plunger from the chamber; and another portion of the plunger may have a locking structure, which cooperates with a locking structure on the chamber to selectively fix the plunger with respect to the chamber. The plunger may also be fully slidable within the chamber when the locking structures of the plunger and the elongate chamber are not engaged. Related methods of using the aforementioned syringe, as well as kits including further instruments that interact with the syringe, are also disclosed.

27 Claims, 15 Drawing Sheets

Locked Plunger

(58) Field of Classification Search
USPC .... 604/64, 187, 188, 218, 220, 224; 606/92, 606/93, 94
See application file for complete search history.

(56) References Cited

U.S. PATENT DOCUMENTS

| | | | | |
|---|---|---|---|---|
| 4,695,382 | A | * | 9/1987 | Cronin ........................ 604/406 |
| 5,389,070 | A | | 2/1995 | Morell |
| 5,468,245 | A | | 11/1995 | Vargas, III |
| 5,681,872 | A | | 10/1997 | Erbe |
| 5,914,356 | A | | 6/1999 | Erbe |
| 5,951,160 | A | * | 9/1999 | Ronk ........................... 366/130 |
| 6,348,055 | B1 | | 2/2002 | Preissman |
| 6,375,659 | B1 | | 4/2002 | Erbe et al. |
| 6,488,649 | B1 | * | 12/2002 | Lichten ......................... 604/64 |
| 6,676,664 | B1 | | 1/2004 | Al-Assir |
| 6,685,668 | B1 | * | 2/2004 | Cho et al. ..................... 604/65 |
| D506,828 | S | | 6/2005 | Layne et al. |
| 7,018,089 | B2 | | 3/2006 | Wenz et al. |
| 2003/0069545 | A1 | * | 4/2003 | Arm ............................. 606/93 |
| 2003/0220648 | A1 | | 11/2003 | Osorio et al. |
| 2004/0196735 | A1 | | 10/2004 | Barker et al. |
| 2005/0027255 | A1 | * | 2/2005 | Lavi et al. .................... 604/135 |
| 2005/0042288 | A1 | | 2/2005 | Koblish et al. |
| 2006/0133193 | A1 | | 6/2006 | Arramon |
| 2006/0164913 | A1 | | 7/2006 | Arramon |
| 2007/0032567 | A1 | | 2/2007 | Beyar et al. |
| 2007/0173949 | A1 | | 7/2007 | Sharps et al. |

FOREIGN PATENT DOCUMENTS

| | | |
|---|---|---|
| WO | WO 2006/079106 A2 | 7/2006 |
| WO | WO 2007/024641 A2 | 3/2007 |
| WO | WO 2007/036815 A2 | 4/2007 |

OTHER PUBLICATIONS

Deramond, H., et al., *Percutaneous Vertebroplasty*, Seminars in Musculoskeletal Radiology, vol. 1, No. 2, 1997: 285-295.

Lewis, G., *Injectable Bone Cements for Use in Vertebroplasty and Kyphoplastry : State-of-the-Art Review*, J. Biomed. Mater. Res. B. Appl. Biomater., Feb. 2006; 76(2): 456-68.

Resnick, D.K. and Garfin, eds. *Vertebroplasty and Kyphoplasty*, 2005 New York: Thieme.

Bernoulli's Equation in Fluid Mechanics. See, e.g., Frank White, *Fluid Mechanics*, 3d ed. McGraw Hill 1994, pp. 335-339.

Orthovita Document No. 5601-0033, Cortoss Brochure (EU), Jul. 17, 2006.

RTG's Viscosity Chart comparing everyday products to cps.

AVAflex™ Curved Injection Needle. CardinalHealth 1 page Copyright 2007.

Office Action from Israeli Application No. 201148, dated Jun. 26, 2011. (English translation of relevant sections only).

International Search Report, PCT/US08/58591, dated Dec. 9, 2008.

* cited by examiner

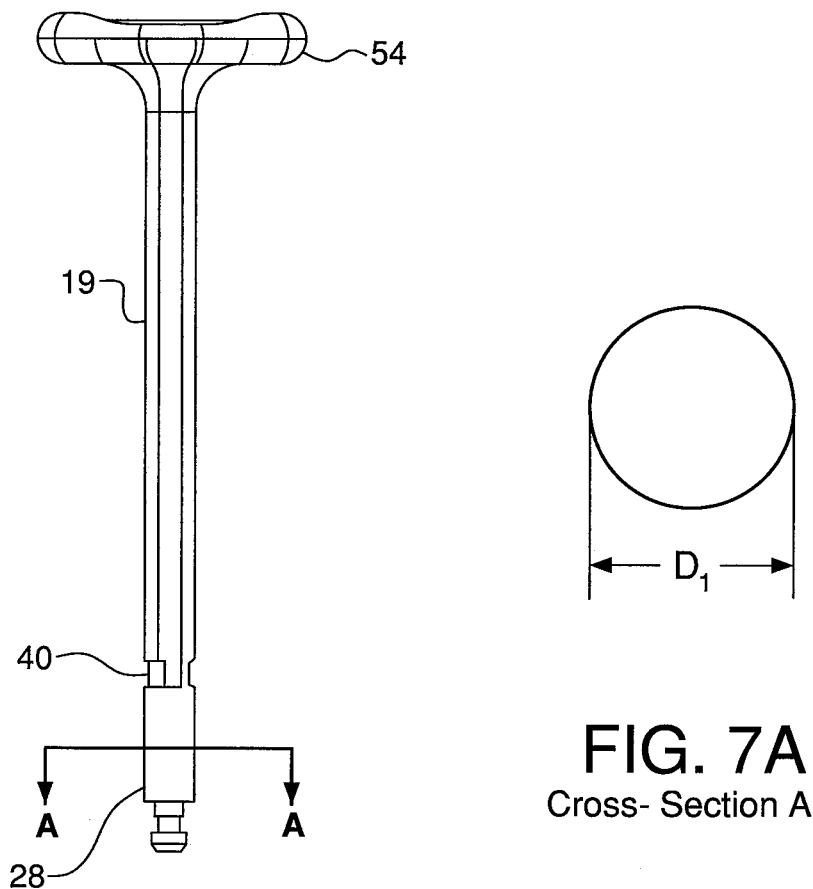
FIG. 7
FIG. 7A
Cross- Section A-A
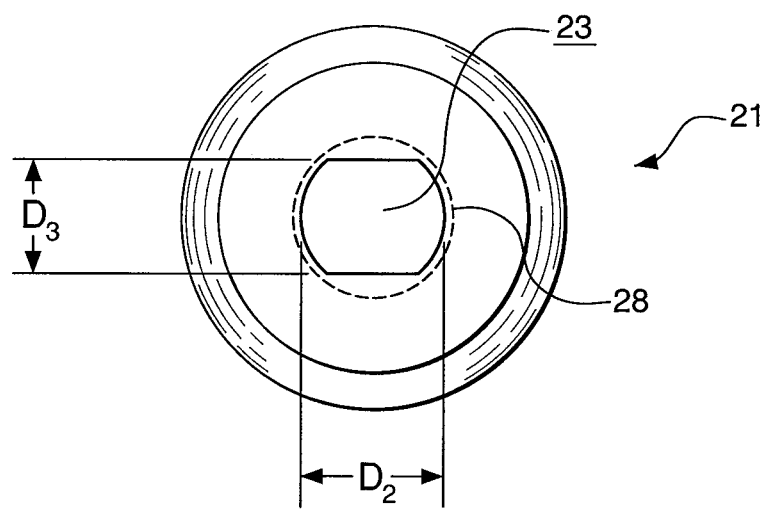
FIG. 8

Unlocked Plunger

Locked Plunger

Cross Section 19

Cross Section 40

Locked

Unlocked

SYRINGE FOR THE DELIVERY OF VISCOUS COMPOSITIONS

CROSS REFERENCE TO RELATED APPLICATIONS

This application claims the benefit of U.S. Provisional Application Nos. 60/909,230 and 60/921,207, filed Mar. 30, 2007, the entireties of which are incorporated herein by reference.

FIELD OF THE INVENTION

The invention described herein relates to devices, kits, and methods of their use, for facilitating delivery of materials into the body, and in particular, for the delivery of bone augmentation material.

BACKGROUND OF THE INVENTION

Percutaneous vertebroplasty (PVP) is a therapeutic procedure that involves injection of bone cement into a vertebral body to confer strength and stability to the vertebra. Kyphoplasty is a related therapeutic procedure. Both procedures are performed minimally invasively and are established techniques for treatment of painful, osteoporotic compression fractures. See, e.g., Gangi, A., et al. *Percutaneous Vertebroplasty Guided by a Combination of CT and Fluoroscopy*, AJNR 15:83-86, January 1994; Deramond, H., et al., *Percutaneous Vertebroplasty*, Seminars In Musculoskeletal Radiology, Vol. 1, No. 2, 1997: 285-295; Resnick, D. K. and Garfin, S. R., *Vertebroplasty and Kyphoplasty*, 2005, each incorporated herein by reference its entirety.

Both procedures have been developed for use with bone cements, for example polymethylmethacrylate (PMMA). Exemplary bone cements include: Confidence Cement System® (Disc-O-Tech, Monroe Township, N.J.), Palacos® Bone Cement (Zimmer, Inc., Warsaw, Ind.), Surgical Simplex®, Spineplex™ (Styker Corp., Kalamazoo, Mich.), KyphX® HV-R™ (Kyphon, Inc., Sunnyvale, Calif.), and Cortoss® (Orthovita, Inc., Malvern, Pa.). (See also, Lewis, G., *Injectable Bone Cements for Use in Vertebroplasty and Kyphoplastry: State-of-the-Art Review*, J. Biomed. Mater. Res. B. Appl. Biomater., 2006 February; 76(2): 456-68). These cements are generally available as two-component systems that, upon mixing, polymerize and harden. As the components polymerize, the viscosity of the resulting composition increases dramatically over a period of a few minutes. Typically, the medical professional has a limited amount of time, once the components are mixed, to load the resulting composition into a syringe, and deliver the composition to the surgical situs, before the composition becomes too viscous to administer. At the same time, the medical professional must be vigilant and avoid leakage of the cement outside of the surgical situs, as such leakage can cause patient injury or fatality.

Devices that reduce the number of steps required to prepare and deliver these cements into the surgical site are needed in order to decrease procedure time and minimize surgical risks to the patient. Reducing the number of steps also provides additional assurances of sterility. In addition, because the procedures are typically carried out under fluoroscopy, devices that remove the physician's hands from the imaging field are needed. Also desirable is an ergonomic device that facilitates hand operation, so that physicians can devote their attention to monitoring the flow of the material into bone.

SUMMARY OF THE INVENTION

The present invention relates to hand- and mechanically-operated devices for composition delivery, comprising an elongate chamber having a lumen; a cap on the proximal end of the chamber having a restricted opening covering the lumen of the chamber; at least one side port having a lumen, the side port lumen being in fluid communication with the lumen of the elongate chamber; and a plunger that is slidable within the lumen of the elongate chamber from a position proximal to conjunction of the lumens of the side port and elongate chamber to a position distal to the conjunction. In preferred embodiments, the axes of the lumens of the chamber and side port form an angle less than 75 degrees. Preferred devices further include an interference member that inhibits removal of the plunger from the elongate chamber and/or a locking structure on the chamber that cooperates with a cooperating locking structure on the plunger when the locking structures are in locking arrangement with one another. The present invention is also directed to kits comprising devices of the present invention and a catheter and/or cannula. Methods of using the devices and kits of the present invention are also described.

BRIEF DESCRIPTION OF THE DRAWINGS

FIG. 7 depicts one embodiment of the plunger of the present invention

FIG. 7A depicts one embodiment of the cross-section of the interference member of the present invention.

FIG. 8 depicts one embodiment of the cap of the present invention. One embodiment of the interference member is shown in phantom lines.

DETAILED DESCRIPTION OF ILLUSTRATIVE EMBODIMENTS

The present invention relates to hand-operated and mechanically-operated devices for the delivery of compositions into a surgical site. Preferably, the devices are capable of delivering viscous compositions, such as bone cements. Bone cements are known in the art and include such materials as polymethylmethacrylate (PMMA). Additional bone cements include Confidence Cement System® (Disc-O-Tech, Monroe Township, N.J.), Palacos® Bone Cement (Zimmer, Inc., Warsaw, Ind.), Surgical Simplex®, Spineplex™ (Styker Corp., Kalamazoo, Mich.), KyphX® HV-R™ (Kyphon, Inc., Sunnyvale, Calif.), and Cortoss® (Orthovita, Inc., Malvern, Pa. described in U.S. Pat. Nos. 5,681,872 and 5,914,356, each of which is incorporated herein by reference). In preferred embodiments of the present invention, the devices are used to deliver bone cement into a vertebral body during vertebroplasty or kyphoplasty.

Bone cements are typically viscous, viscosity being the measure of the internal friction of the material. The greater the internal friction, the great the amount of force, or "shear," required to cause the movement of the material. Methods of measuring viscosity are known in the art. The fundamental unit for viscosity measurements is the poise (ps) or centipoise (cps) (100 ps), water being the standard with a viscosity of 1 cps. Viscous materials used with the present invention can have viscosities of at least 100 cps to over 1,500,000 cps. Preferably, the viscous materials used with the present invention will have viscosities of between about 100 cps to about 400,000 cps. More preferably, the viscous materials used with the present invention will have viscosities of between about 150,000 cps to about 400,000 cps.

The greater the viscosity of the composition being delivered, the greater the force required to effect the delivery. For example, forces exceeding 1000 psi may be required to deliver the composition through the device to the surgical site. As such, devices of the present invention must be comprised of materials capable of withstanding the pressures required for the delivery of the intended viscous material. The devices must also be comprised of materials suitable for sterilization, for example, heat sterilization or gamma sterilization. One exemplary high strength, sterilizable material is polycarbonate.

In addition to being used to deliver viscous materials, the devices of the present invention may also be used to deliver less viscous materials. For example, devices of the present invention can be used to deliver medicaments, such as antibiotics and chemotherapeutics, into the body.

While hand-operated devices of the present invention are preferred, mechanically-operated devices are also envisioned. Methods of mechanical operation are known in the art and include such operations as fluid pressure, levers and linkages, and electric and pneumatic motors.

Figure 19:
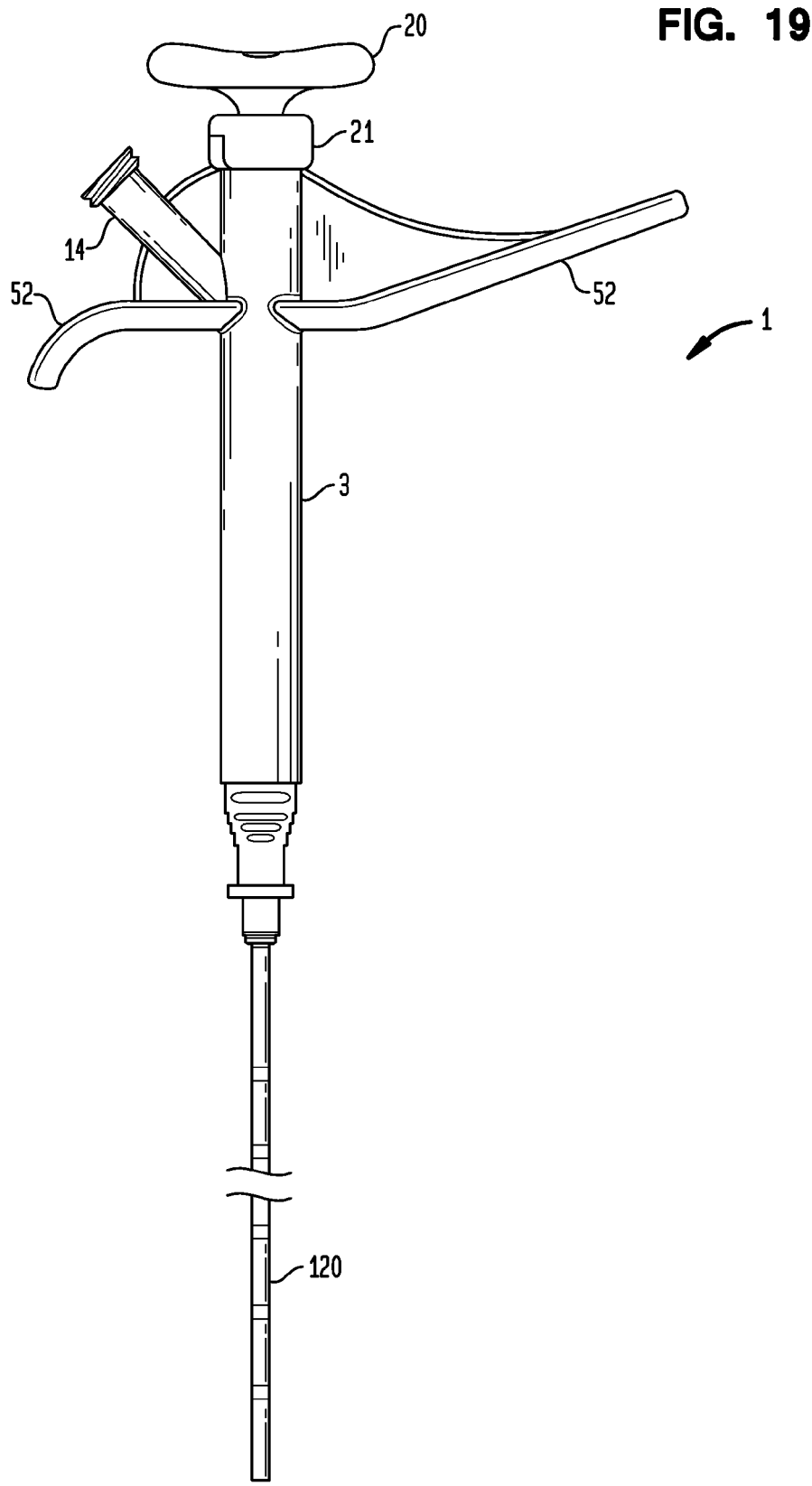
FIG. 19 depicts one embodiment of the present invention comprising a catheter and/or cannula connected to a distal end of the chamber.
Figure 20:
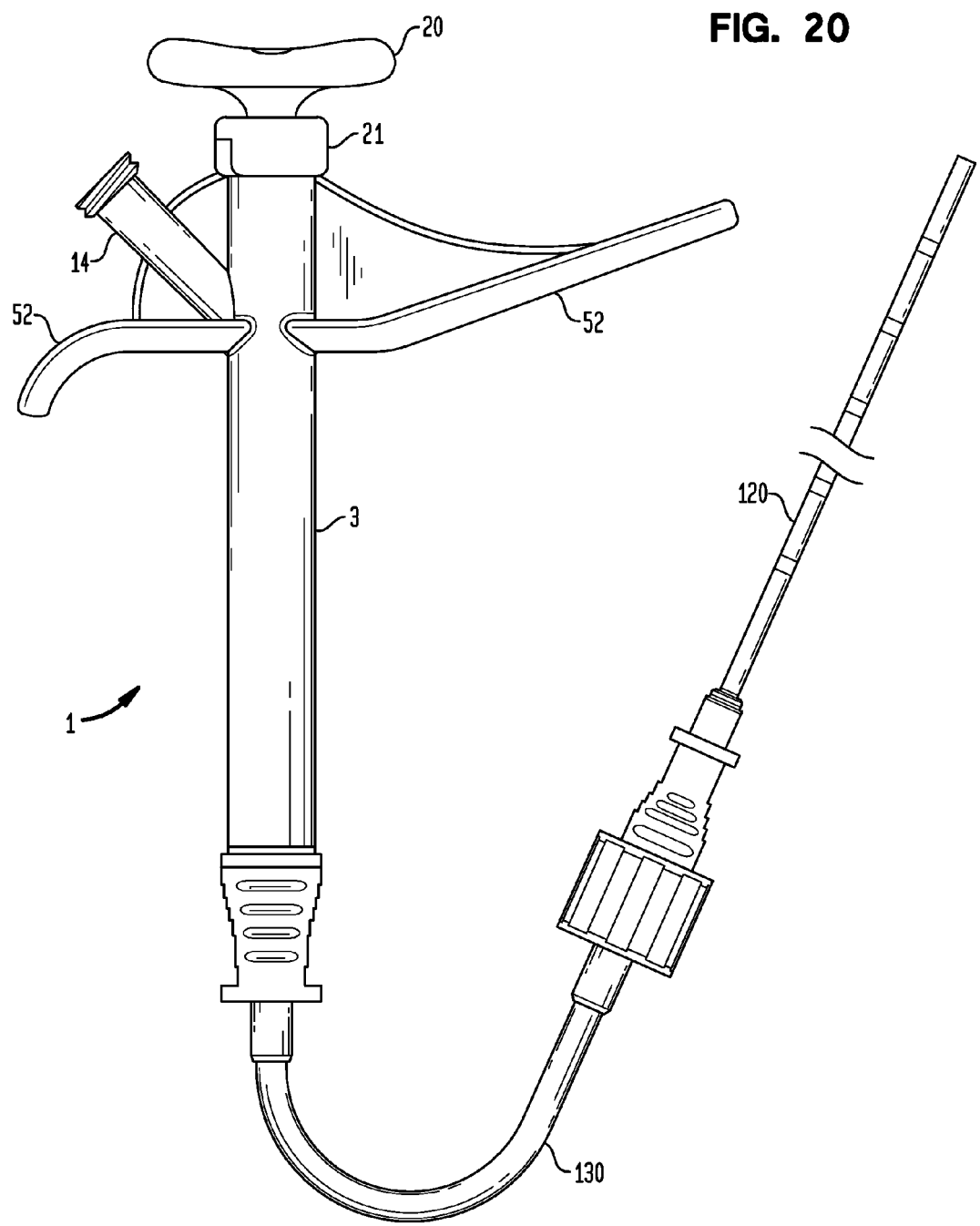
FIG. 20 depicts one embodiment of the present invention comprising an extension member connected to a distal end of the chamber, and a catheter and/or cannula connected to the extension member.

Exemplary embodiments of the present invention are depicted in FIGS. 1-15. Devices of the present invention (1) comprise an elongate chamber 3 having a lumen 7. See FIG. 5, 5A. The elongate chamber has a distal opening 10 through which compositions such as bone cements and medicaments may be delivered. See FIG. 5. The diameter of the distal opening may be equivalent to the diameter of the chamber lumen, or it may be larger or smaller than the diameter of the chamber lumen. In preferred embodiments, the distal opening 10 may further comprise a means for connection of other devices, for example, catheters (e.g., catheter 120 of FIGS. 19-20), cannulas, flexible tubes (e.g., flexible extension 130 of FIG. 20), or needles. Exemplary means for connection include luer fitters and connectors and screw-type connections.

Figure 16:
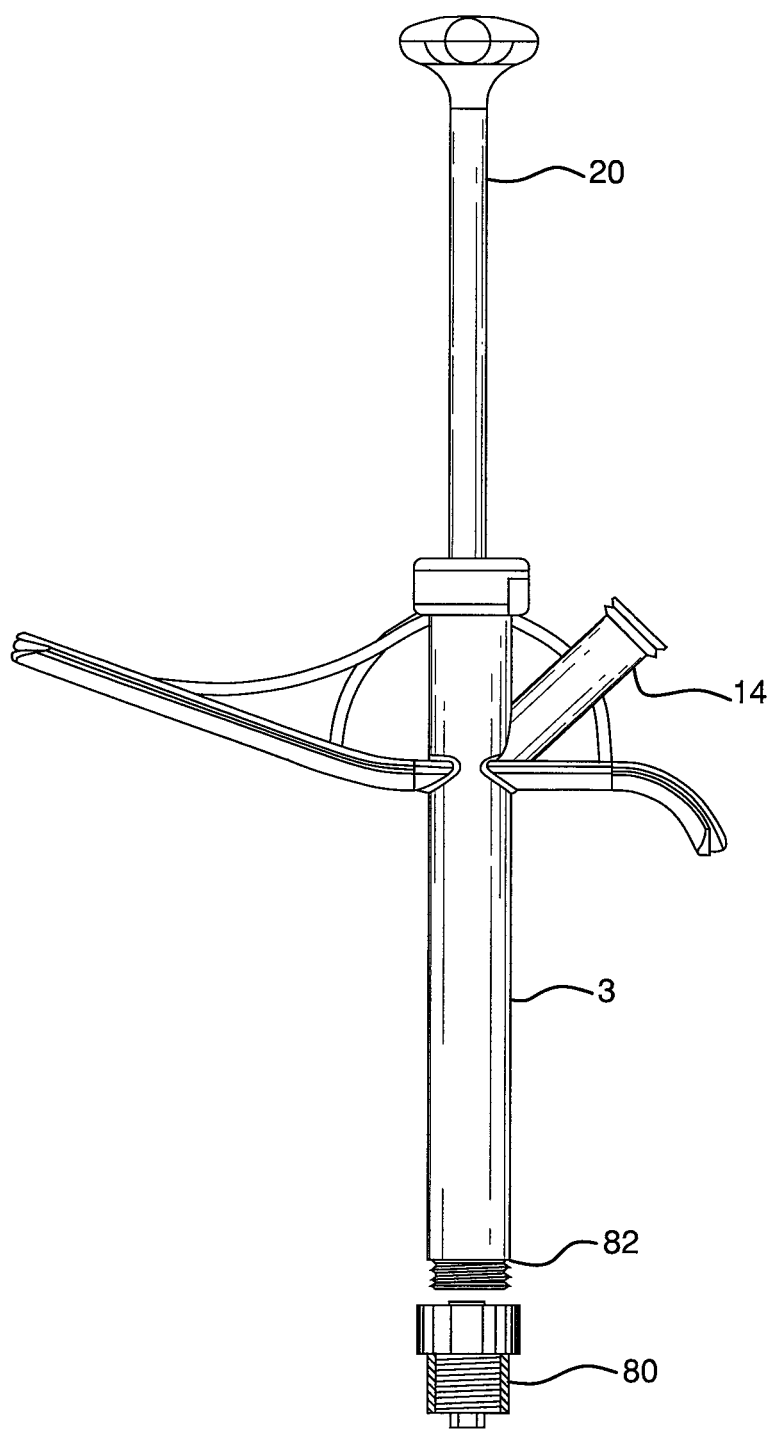
FIG. 16 depicts one embodiment of the present invention comprising a removable end-cap.

In certain embodiments, the distal opening may reside within a removable end-cap (80). Preferably, the end-cap and the distal end of the chamber comprise means for attachment and detachment, for example, complementary threads (82) to allow for the end-cap to be screwed off and on to the distal end of the chamber. FIG. 16 In these embodiments, the end-cap can be removed from the distal end of the chamber to facilitate the ingress and egress of medicaments, radiopacifiers, bone marrow aspirate, plasma, and the like, into the lumen of the chamber.

In other preferred embodiments, devices such as catheters, cannulas, flexible tubes, or needles are integral with the distal opening of the elongate chamber. In those embodiments further comprising a flexible tube, such as flexible extension 130 of FIG. 20, it is envisioned that the flexible tube comprises means for connection of further devices, for example, catheters or cannulas (e.g., catheter 120). Such embodiments allow the medical professional to deliver compositions with devices of the present invention at increased distances, and/or more ergonomic positions from the patient and/or radiation source.

It may be desirable that the body of the elongate chamber is comprised of a translucent or a transparent material in order to facilitate the visualization of materials within the lumen of the elongate chamber. In other embodiments, an elongate chamber may be comprised of an opaque material. In such embodiments, the elongate chamber may further comprise an indicator for assessing the contents of the chamber. The chamber may also comprise markings to indicate the volume of material displaced from the elongate chamber. The chamber may also comprise a handle feature (52).

Devices of the present invention also comprise a cap 21 on the proximal end of the elongate chamber 3, the cap having an opening 23. See FIGS. 4, 4A, 8-10, 13. The opening may have any shaped cross-section. Preferably, the cross-section of the opening is generally circular or generally ovoid. In certain embodiments, the opening has a cross-section that is the same shape as the cross-section of the shaft 19 of plunger 20. See FIGS. 4, 11-13. In preferred embodiments, the opening 23 has a largest diameter that is smaller than the diameter of the lumen 7.

Figure 1:
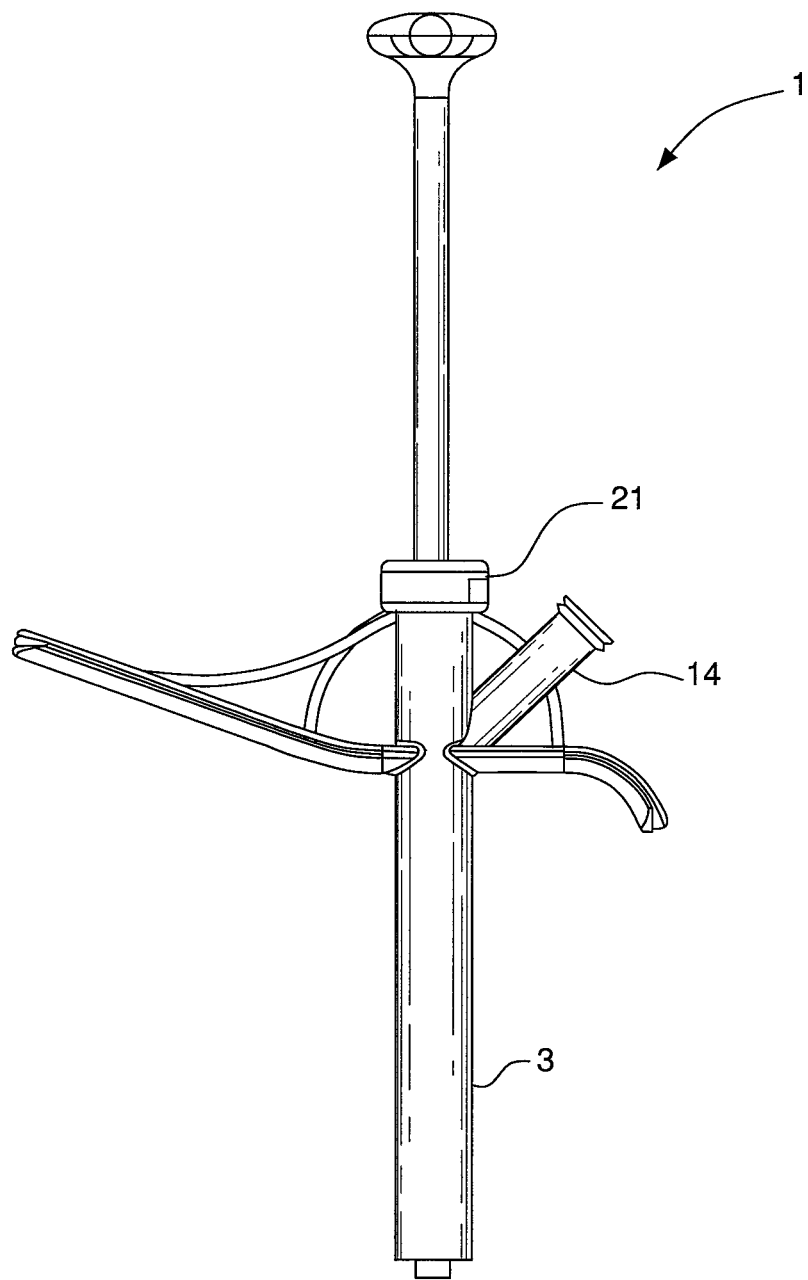
FIG. 1 depicts one embodiment of a device of the present invention comprising an elongate chamber, a cap, a side port, and a plunger.
Figure 2:
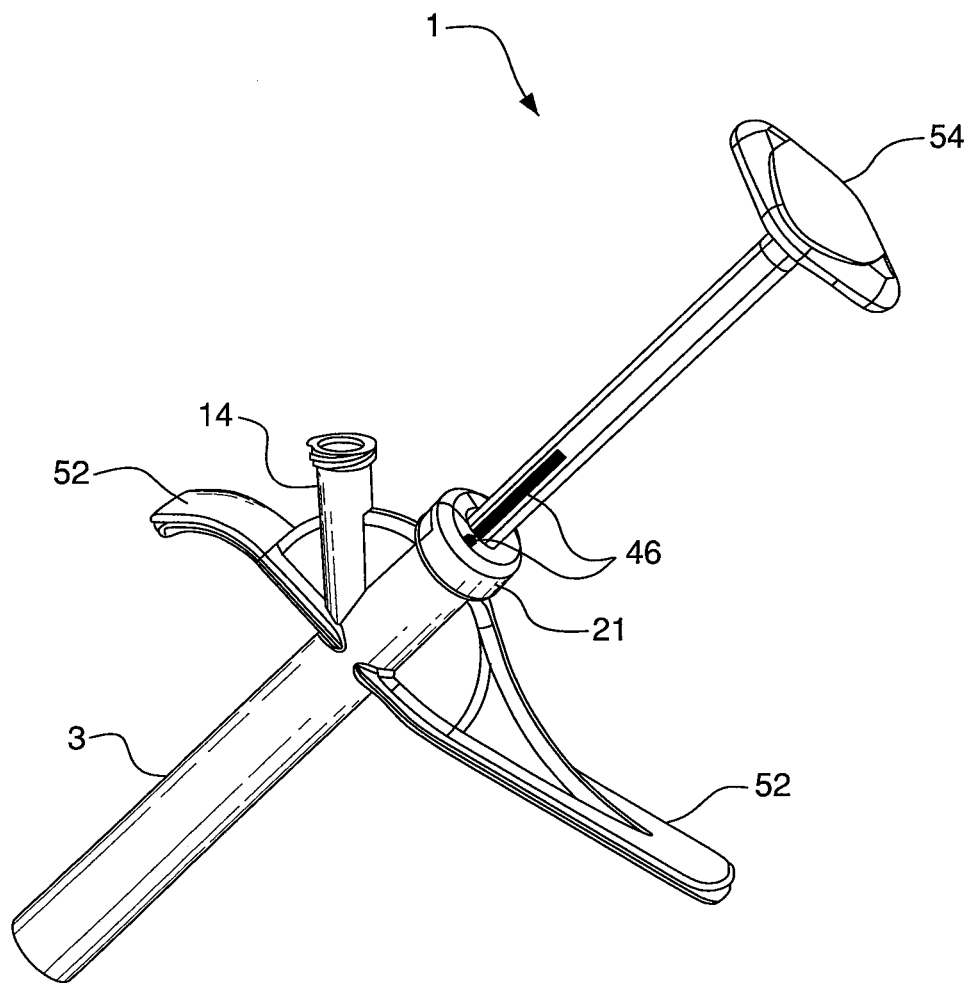
FIG. 2 depicts another embodiment of the present invention having markings.
Figure 3:
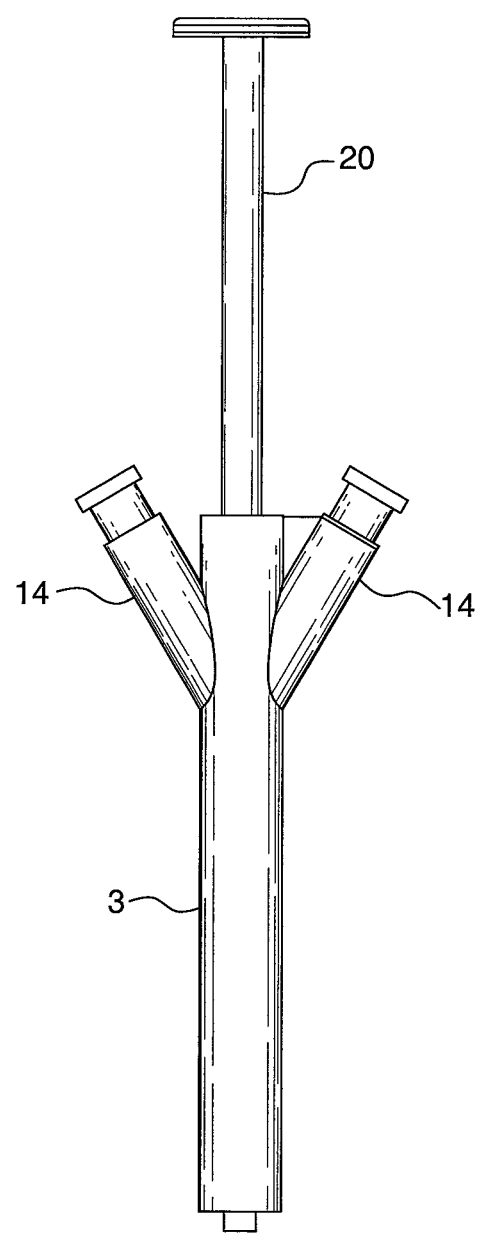
FIG. 3 depicts an embodiment of the present invention comprising two side ports.
Figure 4:
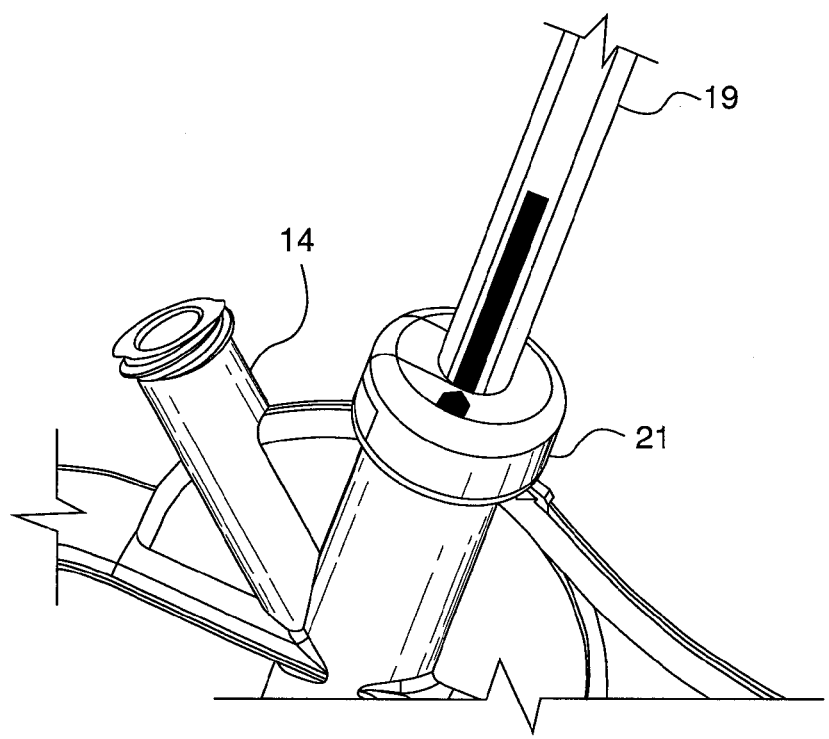
FIG. 4 depicts a view of the proximal end of the chamber, cap, side port, and plunger shaft of one embodiment of the present invention.
Figure 4A:
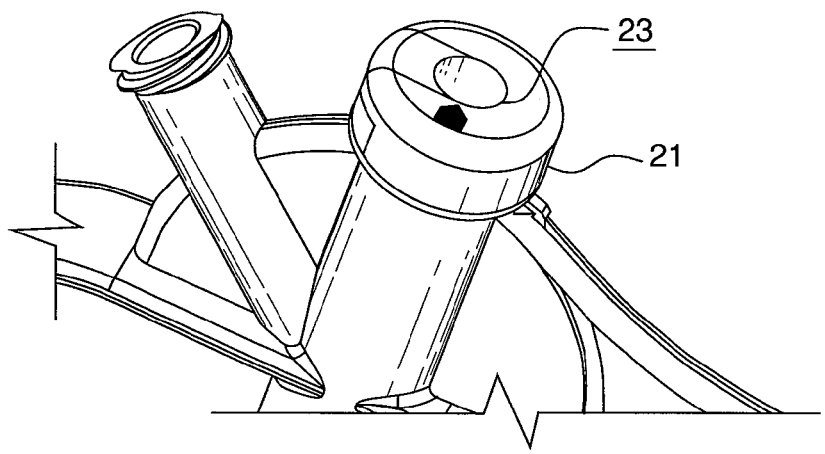
FIG. 4A depicts a view of the proximal end of the chamber, cap, cap opening, and side port of one embodiment of the present invention.
Figure 5:
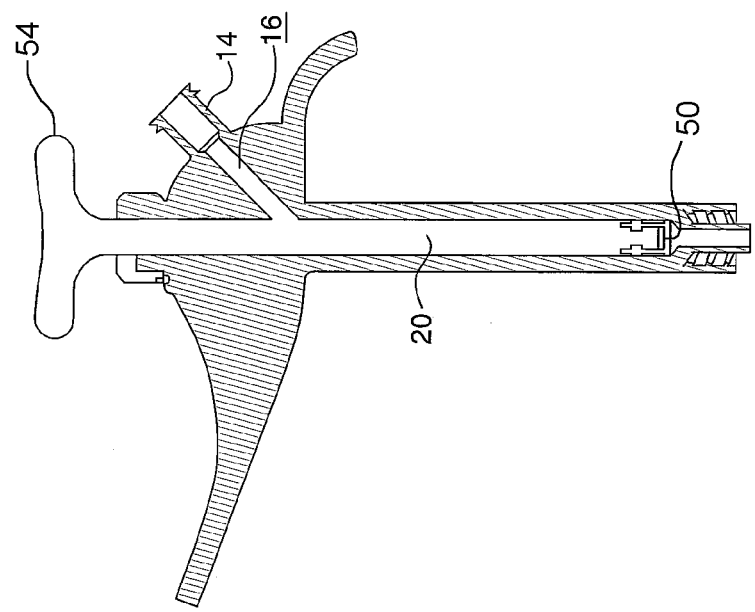
FIG. 5 depicts a cross-sectional view of one embodiment of the present invention wherein the plunger is in a position proximal to the conjunction of the chamber and side port lumens.
Figure 6:
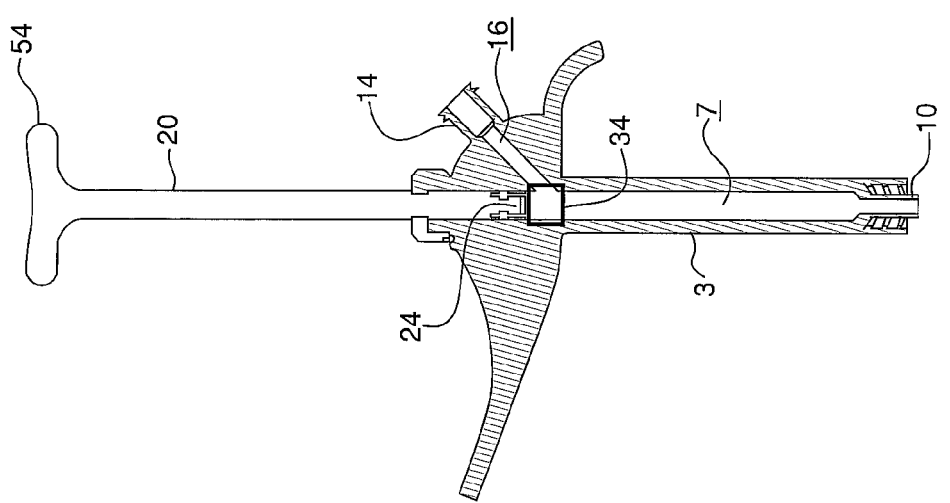
FIG. 6 depicts a cross-sectional view of one embodiment of the present invention wherein the plunger is in a position distal to the conjunction of the chamber and side port lumens.
Figure 5B:
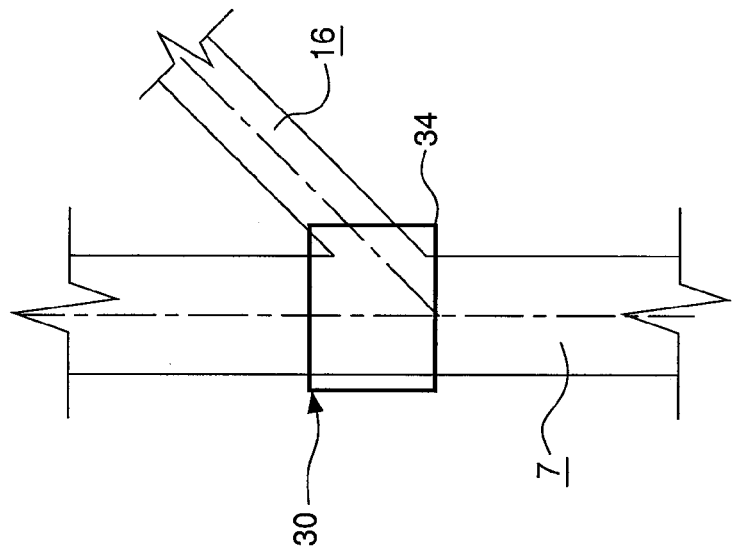
FIG. 5B depicts a cross-sectional view of the conjunction of the chamber and side port lumens.
Figure 5A:
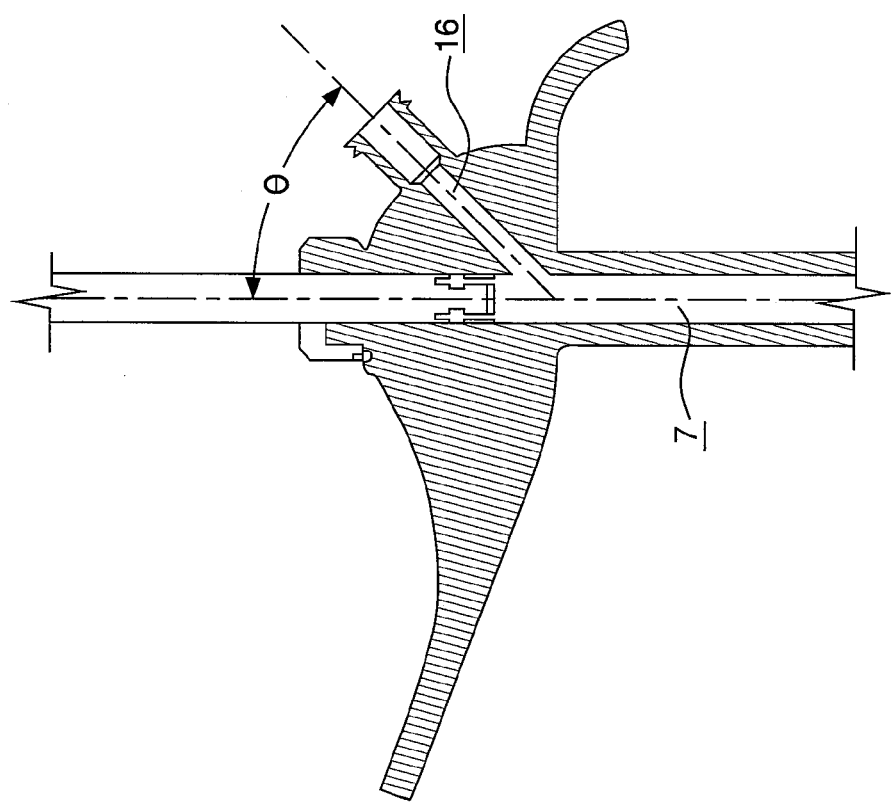
FIG. 5A depicts a cross-sectional view of one embodiment of the present invention depicting θ.
Figure 10:
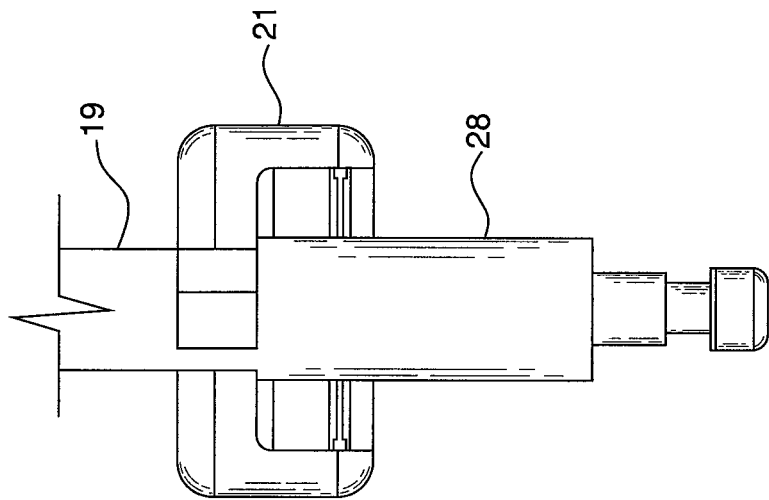
FIG. 10 depicts a cut-away view of one embodiment of the present invention wherein the plunger is in an "unlocked" position.
Figure 9:
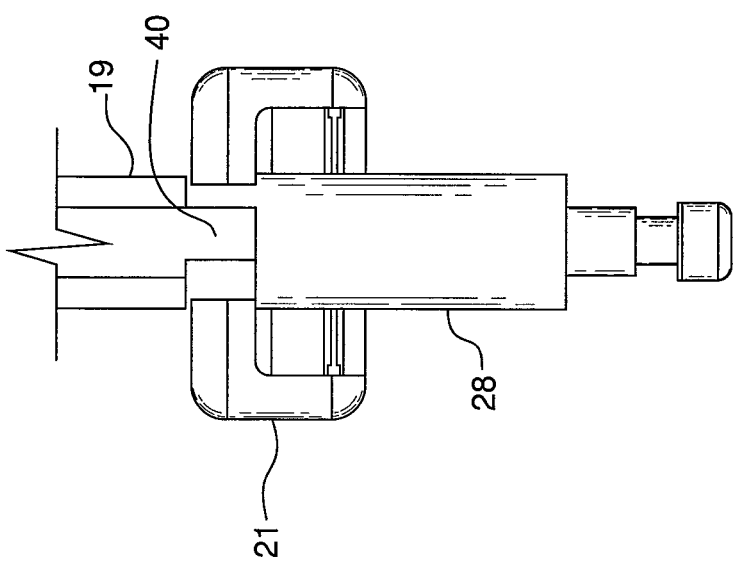
FIG. 9 depicts a cut-away view of one embodiment of the present invention wherein the plunger is in a "locked" position.
Figure 13:
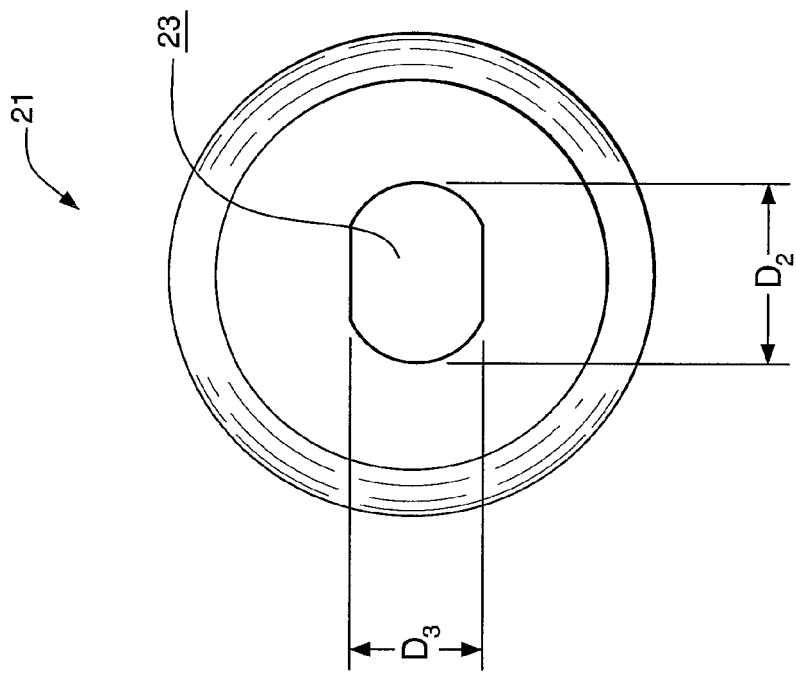
FIG. 13 depicts one embodiment of the cap of the present invention.

The devices of the present invention also comprise at least one side port 14 having a lumen 16. See FIG. 1-6. In preferred uses of the present invention, materials are introduced into the lumen of the elongate chamber through the lumen of the side port. As such, the lumen of the side port is in fluid communication with the lumen of the elongate chamber, as depicted in FIGS. 5, 5A, and 5B. Some embodiments of the present invention comprise more than one side port. See FIG. 3. For example, it is envisioned in those embodiments having two side ports, a first addition of a viscous material may be introduced into the lumen of the elongate chamber from the first side port and a second addition of a viscous material may be introduced into the lumen of the elongate chamber from the second side port. Alternatively, viscous material may be introduced into lumen 7 through the first side port and other materials, for example, medicaments or saline, may be introduced into lumen 7 through the second side port.

As depicted in FIG. 5A, the axis of the lumen of the elongate chamber (7) and the axis of the lumen of the side port (16) form an angle $\theta$ of less than about 75 degrees. It has been determined that an angle of less than about 75 degrees facilitates the introduction of viscous materials into the elongate chamber. While not wishing to be bound to any particular theory, it is believed that an angle of less than 90 degrees reduces the amount of work required to introduce viscous materials into the elongate chamber from the side port lumen. The work done to a system is governed by Bernoulli's Equation in Fluid Mechanics. See, e.g., Frank White, *Fluid Mechanics*, (3d ed. McGraw Hill 1994). The work needed to introduce viscous materials into the elongate chamber from the side port lumen is reduced when the angle between the lumens is less than about 75 degrees, compared to wherein the angle is greater than 75 degrees. In more preferred embodiments, the angle $\theta$ is less than about 60 degrees. Most preferably, the angle $\theta$ is about 45 degrees.

The side port may be permanently conjoined to the elongate chamber 3. In other embodiments, the side port may be detachable from the elongate chamber, for example, by a luer or screw-type connection. The side port may additionally be adapted for connection to, for example, cannulas, catheters, and/or flexible tubing.

The side port may additionally comprise a mixing element. Such mixing elements are known in the art and may be connected in series with the side port, for example, by a luer or screw-type connection. In other embodiments, the mixing element may reside within the lumen of the side port. In those embodiments wherein the side port is detachable from the elongate chamber, it is envisioned that a mixing element can be connected to the elongate chamber in place of the side port.

In certain embodiments, the side port further comprises a flow regulation element. Such flow regulation elements may be connected in series with the side port or may reside within the lumen of the side port. Flow regulation elements are known in the art and exemplary flow regulation elements include devices such as two-way and three-way stopcocks.

In other embodiments, the side port further comprises at least one filter element. Preferably, the side port further comprises a plurality of filter elements. The filter element may be connected in series with the side port or may reside within the lumen of the side port. Filter elements that remove impurities and sterilize liquids are within the scope of the invention. Such filter elements are known in the art.

Devices of the present invention also comprise a plunger 20. The plunger is slidable within the lumen of the elongate chamber. As used herein, "slidable" refers to the movement of the plunger within the lumen of the elongate chamber by the application of longitudinal force to the plunger. The plunger is slidable within the lumen from a position proximal (30) to the conjunction of the lumens of the side port and elongate chamber (34) to a position distal to the conjunction of the lumens. See FIGS. 5, 5A, 6. In exemplary embodiments of the invention, the plunger, when in a position proximal to the conjunction of the lumens, will not impede the introduction of materials from the lumen of the side port to the lumen of the elongate chamber. See FIG. 5, 5A. It may also be desirable that the plunger distal end (24) further comprises a tip (50) that forms a compression seal when engaged within the elongate chamber. The plunger may also comprise a handle feature 54. The handle 54 is ergonomically designed to provide for one-handed operation of the plunger.

Figure 17:
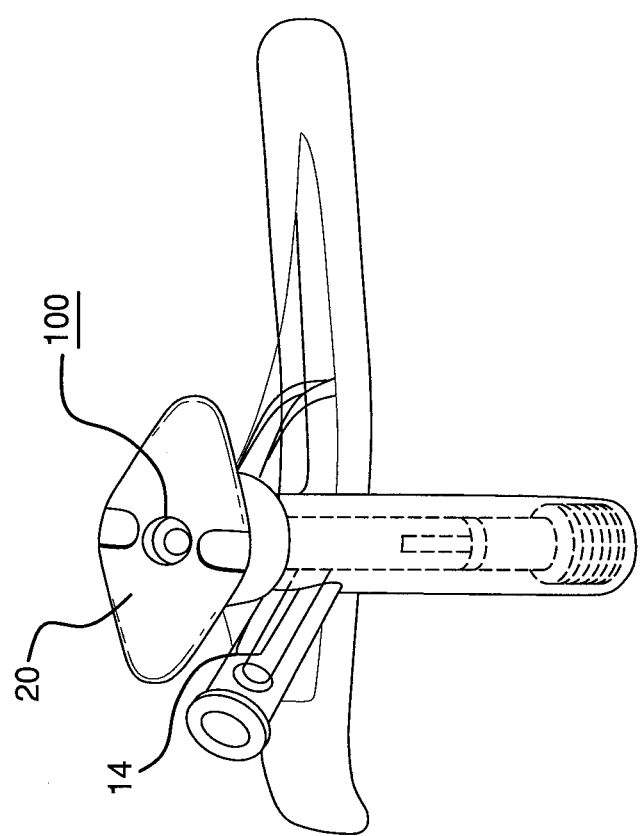
FIG. 17 depicts one embodiment of the present invention depicting one embodiment of the present invention comprising a plunger lumen.
Figure 18:
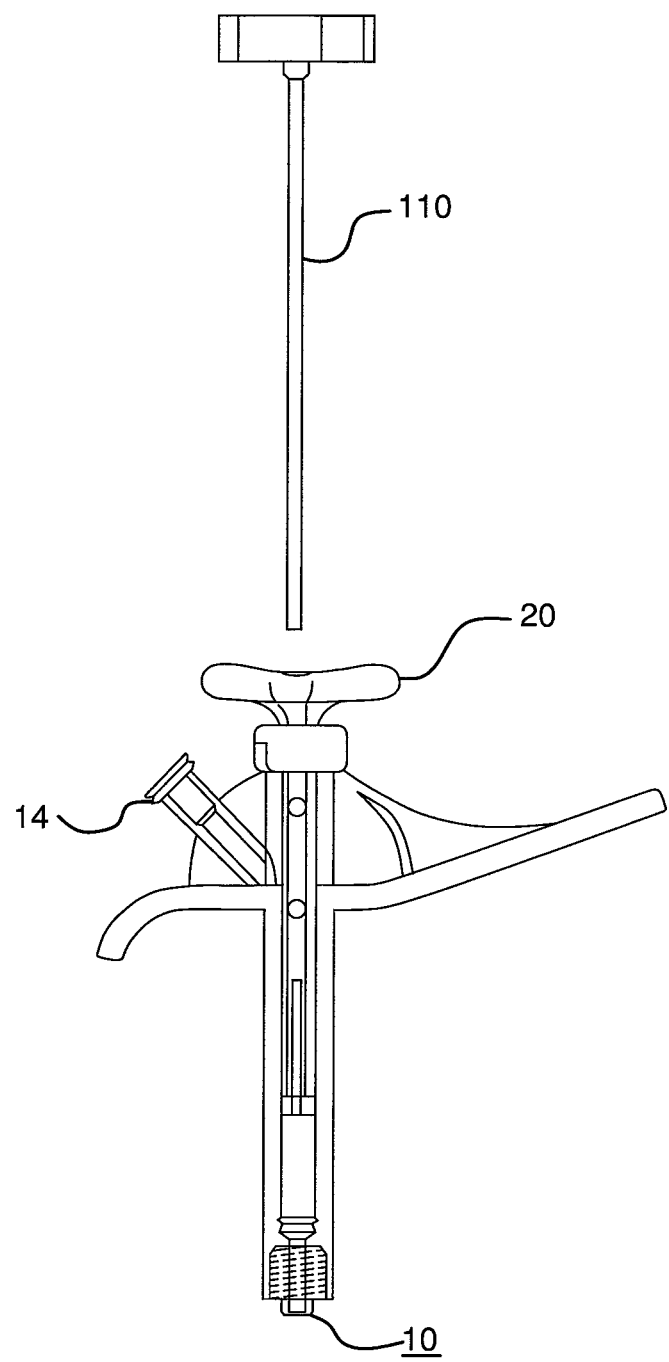
FIG. 18 depicts one embodiment of the present invention depicting one embodiment of the present invention comprising a plunger lumen and plunger insert.

In certain embodiments, the plunger may additionally comprise a lumen (100). See FIGS. 17 and 18. In such embodiments, the plunger lumen is configured to be capable of being in fluid communication with the lumen of the elongate chamber. In some embodiments, the plunger lumen may further include a penetrable barrier, such that penetration of the barrier engages fluid communication between the plunger lumen and the elongate chamber. This barrier may reside at any position along the longitudinal axis of the plunger lumen. Penetration of the barrier may be effected by puncturing, rupturing, dissolution, and/or removal of the barrier. Examples of such penetrable barriers are known in the art and include, for example, gaskets, seals, and the like. Dissolvable barriers are those that dissolve in aqueous and/or organic liquids or solvents and include, for example, those comprised of polylactic acid, polysaccharides, and/or monosaccharides. Dissolvable barriers may also include those comprising PMMA.

Preferably, the lumen of the plunger is sized such that viscous and/or non-viscous materials may be introduced into the lumen of the elongate chamber through the lumen of the plunger. In other embodiments, the lumen of the plunger can be used to introduce other medical instruments, for example, guide wires, trocars, and the like, through the elongate chamber and through the distal opening 10 of the device.

In certain of those embodiments wherein the plunger comprises a lumen, a plunger insert (110) may be provided that is sized such that when the plunger insert is within the plunger lumen, advancement of the plunger/plunger insert results in the displacement of viscous and/or non-viscous materials along the lumen of the elongate chamber and through the distal opening 10. In certain embodiments, the plunger insert comprises means to lock and unlock the plunger insert within the plunger lumen.

The plunger 20 may further comprise an interference member 28. See FIGS. 7, 9-10. The interference member inhibits the removal of the plunger from the elongate chamber of the device. Preferably, the interference member inhibits the removal of the plunger through the opening 23 of cap 21. In preferred embodiments, the interference member is shaped such that at least one diameter of the cross-section of the interference member is greater than the largest diameter of the opening 23 of the cap, such that the interference member cannot move through the opening 23. In certain embodiments, the interference member has a cross-section having a diameter $D_1$ (see FIG. 7-7A) and the opening of the cap has a cross-section having a diameter $D_2$, wherein $D_1$ is greater than $D_2$. See FIG. 8. In other preferred embodiments, the opening of the cap has an irregular cross-section having at least diameters $D_2$ and $D_3$ (see, for example FIG. 8). In such embodiments, $D_1$ is greater than either or both $D_2$ and $D_3$. Preferably, the interference member has a generally circular cross-section.

Devices of the present invention may also comprise cooperating locking structures on the elongate chamber and the plunger. Exemplary embodiments of such locking structures are depicted in FIGS. 9-15. In preferred embodiments, the cooperation maintains the distal end of the plunger (24) at the position proximal to the conjunction of the side port and elongate chamber lumens (34). See FIGS. 5, 5A. Maintaining the distal end of the plunger at the position proximal to the conjunction of the lumens may be desirable to prevent displacement of the plunger into the conjunction of the lumens while material is being introduced into the lumen of the elongate chamber from the side port.

Figure 12A:
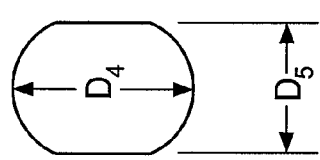
FIG. 12A depicts the cross-section of one embodiment of the plunger shaft of the present invention.
Figure 12B:
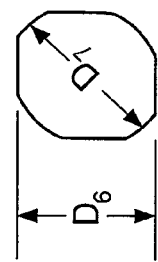
FIG. 12B depicts the cross-section of one embodiment of the rotational element of a plunger of the present invention.
Figure 11:
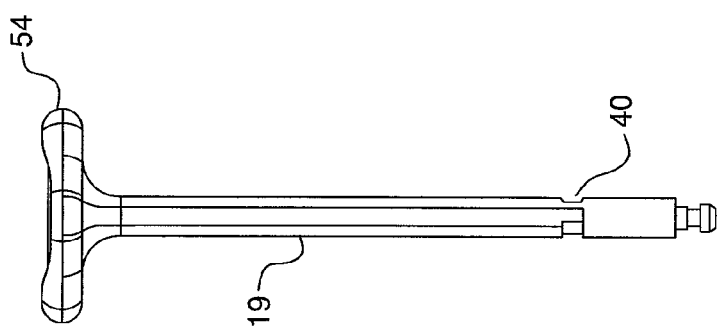
FIG. 11 depicts one embodiment of the plunger of the present invention.
Figure 15:
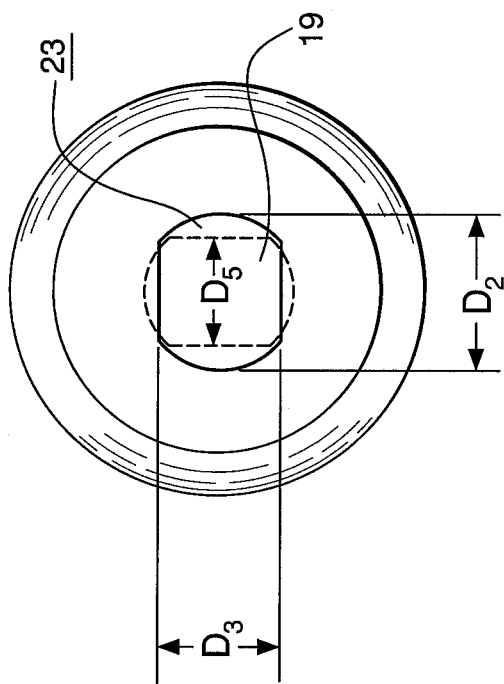
FIG. 15 depicts one embodiment of the present invention wherein the plunger (shown in phantom lines) is in a "locked" position.
Figure 14:
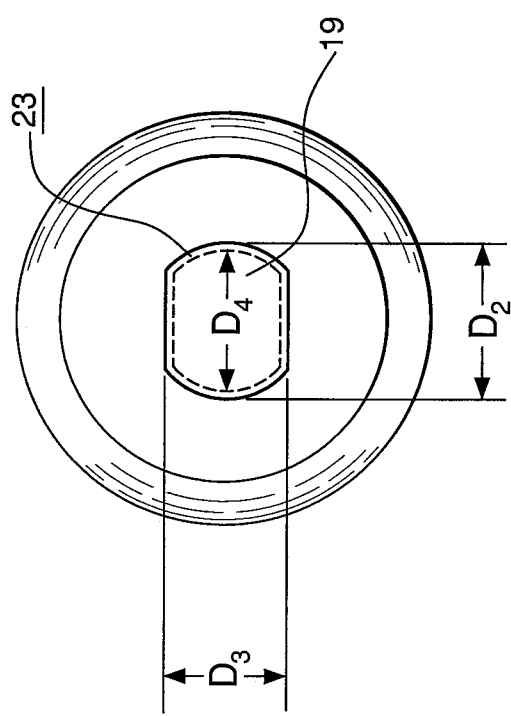
FIG. 14 depicts one embodiment of the present invention wherein the plunger (shown in phantom lines) is in an "unlocked" position.

In preferred embodiments of the present invention, the opening 23 of the cap 21 may perform as a locking structure and cooperate with a locking structure on the plunger. See FIGS. 9-10, 14-15. In preferred embodiments, the plunger locking structure may comprise shaft 19 and rotational element 40 of the plunger. See FIGS. 9-12. For example, the opening 23 may comprise a cross-section having diameters $D_2$ and $D_3$. See FIG. 13. Additionally, the shaft 19 may have a cross-section having diameters $D_4$ and $D_5$. FIG. 12A. Preferably, $D_2$ is approximately equal to $D_4$ and $D_3$ is approximately equal to $D_5$, such that, when $D_2$ and $D_4$ are aligned (see FIG. 14) in an "unlocked" position, the plunger 20 is slidable through the opening 23 and within the elongate chamber lumen 7. Conversely, when the plunger is rotated around its axis such that $D_2$ and $D_5$ are aligned (see FIG. 15) in a "locked" position, the plunger is not slidable through the opening and is maintained in the "locked" position. In preferred embodiments, the elongate chamber and the plunger have markings (46) to indicate whether the plunger is in the "locked" or "unlocked" position. See FIG. 4.

To provide for rotation of the plunger within the device, the plunger may further comprise rotational element 40 having a cross-section with at least one diameter, $D_6$. See FIG. 9-11, 12B. The rotation element is sized such that when it is within the opening 23, the plunger is rotatable within the device. In preferred embodiments, the rotational element is shaped and sized such that when the plunger is rotated while rotational element 40 is within opening 23, the rotational element provides tactile or auditory feedback to the device user. Such feedback may signal to the user when the plunger is in a "locked" or "unlocked" position. In exemplary embodiments of the present invention, the rotational element has at least two diameters, $D_6$ and $D_7$. See FIG. 12B. Preferably, $D_6$ has a diameter that is smaller than the diameter of $D_3$ and $D_7$ has a diameter that is slightly larger than $D_3$. See FIGS. 12B-13. In such embodiments, $D_7$ is sufficiently large such that there is moderate resistance of the rotation of the plunger when the rotational element 40 is within opening 23. The moderate resistance is such that it may be overcome by manual force to allow for rotation of the plunger when rotational element 40 is within 23. Such resistance provides a tactile and/or auditory signal to the user that the plunger is being rotated a certain distance within the opening 23. In certain embodiments, the resistance provides a tactile and/or auditory signal that the plunger has been rotated about 90 degrees. In other embodiments, the resistance provides a tactile and/or auditory signal that the plunger has been rotated about 180 degrees.

In certain embodiments of the present invention, at least one of the elongate chamber, side port, and plunger are comprised of flexible, non-compliant material. In some embodiments, the elongate chamber and plunger are comprised of flexible, non-compliant material. In such embodiments, the device would yield to transversely applied pressure to facilitate maneuverability and delivery of compositions into the surgical site. Such embodiments can further increase the distance of the device and the medical professional from the radiation source.

In other embodiments of the present invention, the elongate chamber may be curved or angled to facilitate maneuverability, composition delivery, and distance from the radiation source. In such embodiments, the elongate chamber may be comprised of flexible, non-compliant or rigid material. The plunger for use in such embodiments may also be either of rigid or flexible, non-compliant material.

Using the skill of one in the art, devices of the present invention may be sized to accommodate any pre-selected volume of material. In some embodiments, the devices of the present invention may be sized to accommodate up to 60 $cm^3$. Preferably, the devices can accommodate from about 1 $cm^3$ to about 30 $cm^3$. It is also envisioned that volumes of about 0.25 $cm^3$ and about 0.5 $cm^3$ can also be accommodated. In certain embodiments, the devices may be sized to accommodate up to about 5, 10, or 20 $cm^3$. In other embodiments, the devices may accommodate about 1.5 $cm^3$. Most preferred embodiments may accommodate about 1 $cm^3$.

Also within the scope of the present invention are kits comprising a hand- or mechanically-operated device for the delivery of a composition, the device comprising an elongate chamber having a lumen; a cap on the proximal end of the chamber having a restrictive opening covering the lumen of the chamber; at least one side port having a lumen, said side port lumen being in fluid communication with the lumen of the elongate chamber, the axes of the lumens of the chamber and side port forming an angle less that 75 degrees; and a plunger slidable within the lumen of the elongate chamber from a position proximal to conjunction of the lumens of the side port and elongate chamber to a position distal to the conjunction. In some kits of the present invention, the plungers of the devices further comprise an interference member that inhibits removal of the plunger from the elongate chamber. In other kits of the present invention, the elongate chambers of the devices further comprise a locking structure that cooperates with a cooperating locking structure on the plunger when the locking structures are in a locking arrangement with one another. Preferably, the devices comprise plungers comprising an interference member that inhibits removal of the plunger from the device and elongate chambers comprising a locking structure that cooperates with a cooperating locking structure on the plunger when the locking structures are in a locking arrangement with one another.

In addition to the device, kits of the present invention further include at least one catheter and/or cannula. Catheters and cannulas used in the kits may comprise stainless steel, polyimide, latex, silicone, vinyl, or other polymer suitable in the art. They may be rigid or they may be flexible for maneuverability and be long and of such material that they can be cut to size at the time of use.

Kits of the present invention may also comprise at least one flexible extension adapted for connection to the side port and/or the elongate chamber. Flexible extensions used in the kits may comprise latex, silicone, vinyl, or other polymer suitable in the art.

Additionally, the kits of the present invention may comprise a reamer for creating an access path to a vertebral body or intraosseous space. Reamers used in the kits may comprise stainless steel, titanium, or other polymer suitable in the art. The kits may also comprise needles and stylets adapted for piercing cortical bone.

The instant invention is illustrated by the following example that is not intended to limit the scope of the invention.

EXAMPLE

A needle/stylet is inserted into bone using gentle tapping and/or pushing. The stylet is removed and a reamer is inserted through the needle. The reamer is advanced through the needle and then removed.

A device of the present invention is attached to a catheter at the distal end of the elongate chamber. The plunger of the device is extended to the position proximal to the conjunction of the lumens of the side port and the elongate chamber and rotated around its axis to lock the plunger in position. A gun and mix-tip assembly is attached to the side port and bone augmentation material is introduced into the lumen of the elongate chamber of the device via the side port. Filling through the side port continues until both the container and the attached catheter are filled with the desired amount of bone augmentation material. The gun and mix-tip are removed from the side port. The catheter is inserted into the bone through the needle. The plunger is rotated around its axis to unlock the plunger and the bone augmentation material is dispensed into bone by the application of longitudinal pressure to the plunger.

Certain of these steps may be repeated, if necessary, to deliver the desired amount of bone augmentation material into the bone.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed:

1. A device for the delivery of a composition, the device comprising:
    (a) an elongate chamber having a lumen;
    (b) a cap on the proximal end of the chamber having a restricted opening, the cap covering at least a portion of the lumen of the chamber;
    (c) at least one side port having a lumen, said side port lumen being in fluid communication with the lumen of the elongate chamber; and
    (d) a plunger having a plunger seal slidable in sealing engagement within the lumen of the elongate chamber from a position proximal to conjunction of the lumens of the side port and elongate chamber to a position distal to said conjunction;
    (e) the plunger having an interference member that inhibits removal of the plunger from the elongate chamber through the restricted opening; and
    (f) the elongate chamber having a locking structure that is engageable and disengageable with a corresponding locking structure on the plunger, wherein engagement between the locking structures of the elongate chamber and the plunger locks the plunger and its plunger seal relative to the elongate chamber, and disengagement between the locking structures of the elongate chamber and the plunger unlocks the plunger and its plunger seal relative to the elongate chamber so that the plunger and its plunger seal are movable within the elongate chamber.

2. The device of claim 1, wherein the axes of the lumens of the chamber and side port form an angle of about 60 degrees to 75 degrees.

3. The device of claim 1, wherein the axes of the lumens of the chamber and side port form an angle of about 45 degrees.

4. The device of claim 1, wherein the engaging and disengaging results from rotation of the plunger around a longitudinal axis of the plunger.

5. The device of claim 1, wherein the engaging maintains a distal end of the plunger at the position proximal to conjunction of the lumens.

6. The device of claim 1, wherein the side port further comprises a flow regulation element.

7. The device of claim 1, wherein the side port is detachable from the chamber.

8. The device of claim 1, wherein the side port further comprises at least one filter element.

9. The device of claim 1, wherein the chamber is comprised of a translucent or a transparent material.

10. The device of claim 1, wherein the chamber further comprises an indicator for assessing the contents of the chamber.

11. The device of claim 1, wherein at least one of the elongate chamber, plunger, and side port are comprised of generally flexible material.

12. The device of claim 1, wherein the chamber and the plunger further comprise handles.

13. The device of claim 1, wherein a composition inserted into the elongate chamber includes a viscosity that is between 100 centipoise and 400,000 centipoise.

14. The device of claim 1, wherein a composition inserted into the elongate chamber includes a viscosity that is between 150,000 centipoise and 400,000 centipoise.

15. The device of claim 1 comprising two side ports.

16. The device of claim 1, further comprising at least one cannula or catheter.

17. The device of claim 16, wherein the cannula or catheter is fixably attached to the elongate chamber.

18. The device of claim 1, wherein the plunger comprises a lumen.

19. The device of claim 18, further comprising a penetrable barrier within the plunger lumen.

20. The device of claim 18, further comprising a plunger insert.

21. A device for the delivery of a composition, the device comprising:
    (a) an elongate chamber having a lumen;
    (b) a cap on the proximal end of the chamber having a restricted opening, the cap covering at least a portion of the lumen of the chamber;
    (c) at least one side port having a lumen, said side port lumen being in fluid communication with the lumen of the elongate chamber;
    (d) a plunger having a plunger seal slidable in sealing engagement within the lumen of the elongate chamber from a position proximal to conjunction of the lumens of the side port and elongate chamber to a position distal to said conjunction;
    (e) a locking structure on the elongate chamber that is engageable and disengageable with a corresponding locking structure on the plunger, wherein engagement between the locking structures of the elongate chamber and the plunger locks the plunger and its plunger seal relative to the elongate chamber in a locked position, and disengagement between the locking structures of the elongate chamber and the plunger unlocks the plunger and its plunger seal relative to the elongate chamber so that the plunger and its plunger seal are movable within the elongate chamber; and
(f) a rotational element on the plunger which, when the plunger is in the locked position, indicates to a user of the device that the plunger is in the locked position;
(g) the plunger having an interference member that cooperates with the restricted opening to inhibit removal of the plunger from the elongate chamber through the restricted opening.

22. The device of claim 21, wherein the rotational element, when rotated to the locked position, provides tactile or auditory feedback to the user that indicates the plunger is in the locked position.

23. The device of claim 21, wherein a dimensional interference between the rotational element and a portion of the elongate chamber indicates to the user of the device that the plunger is in the locked position.

24. The device of claim 23, wherein the dimensional interference provides both auditory and tactile feedback to the user to indicate that the plunger is in the locked position.

25. A device for the delivery of a composition, the device comprising:
(a) an elongate chamber having a lumen;
(b) a cap on the proximal end of the chamber having a restricted opening, the cap covering at least a portion of the lumen of the chamber;
(c) at least one side port having a lumen, said side port lumen being in fluid communication with the lumen of the elongate chamber; and
(d) a plunger having a plunger seal slidable in sealing engagement within the lumen of the elongate chamber from a position proximal to conjunction of the lumens of the side port and elongate chamber to a position distal to said conjunction;
(e) the elongate chamber having a locking structure that is engageable and disengageable with a corresponding locking structure on the plunger, wherein engagement between the locking structures of the elongate chamber and the plunger locks the plunger and its plunger seal relative to the elongate chamber, and disengagement between the locking structures of the elongate chamber and the plunger unlocks the plunger and its plunger seal relative to the elongate chamber so that the plunger and its plunger seal are movable within the elongate chamber.

26. The device of claim 25, wherein the plunger further comprises an interference member that inhibits removal of the plunger from the elongate chamber.

27. The device of claim 25, wherein the axes of the lumens of the chamber and side port form an angle less than 75 degrees.

* * * * *